United States Patent [19]

Corey et al.

[11] Patent Number: 5,187,104

[45] Date of Patent: Feb. 16, 1993

[54] NITRO OR NITROSO SUBSTITUTED POLYHALOGENATED PHENOLSULFONEPHTHALEINS AS PROTEIN INDICATORS IN BIOLOGICAL SAMPLES

[75] Inventors: Paul F. Corey; Angela A. Michaels, both of Elkart; Lois J. Proud, Granger, all of Ind.; Michael Salvati, St. Paul, Minn.; Robert W. Trimmer, Germantown, Md.; Ronald G. Sommer, Elkart, Ind.

[73] Assignee: Miles Inc., Elkart, Ind.

[21] Appl. No.: 710,952

[22] Filed: Jun. 6, 1991

[51] Int. Cl.$^5$ ............................................. C01N 33/00
[52] U.S. Cl. ...................................................... 436/86
[58] Field of Search ........................................... 436/86

[56] References Cited

U.S. PATENT DOCUMENTS 4,054,450  10/1977  Schoustra et al. ..................... 96/1 R

FOREIGN PATENT DOCUMENTS 2432388  1/1975  Fed. Rep. of Germany .

OTHER PUBLICATIONS

Y. Nagase et al. Ann. Proc. Gifu Coll. Pharma. No. 4, 44–50. (1954).

*Primary Examiner*—John W. Rollins
*Attorney, Agent, or Firm*—Roger N. Coe

[57] ABSTRACT

The present invention provides a novel group of protein error indicators including nitro or nitroso substituent groups in the B and C rings of a partially halogenated triphenylmethane compound.

11 Claims, 6 Drawing Sheets

NITRO OR NITROSO SUBSTITUTED POLYHALOGENATED PHENOLSULFONEPHTHALEINS AS PROTEIN INDICATORS IN BIOLOGICAL SAMPLES

BACKGROUND OF THE INVENTION

A. Field of the Invention

The present invention is related generally to the detection of protein in biological samples; and more particularly, to a novel method for the determination of protein in a biological sample using novel protein error indicators.

B. Description of the Background Art

Determining the presence of protein in a biological sample is of utmost importance in the diagnosis of several pathological conditions affecting the kidney, circulatory system, and central nervous system. Frequently, it is necessary to qualitatively and quantitatively measure protein (albumin) in urine. This is especially important in the diagnosis of diabetes, urinary tract infection, and kidney disease. The predominant protein in diabetes and kidney disease is albumin; hence the model system for protein urine testing is albumin.

Methods for determining the presence of albumin in urine are well known. The most inexpensive and convenient method for albumin determination involves wetting a paper test strip with a small quantity of urine. The test strip is impregnated with a protein error indicator. If albumin is present in the sample, the test strip will indicate this by simply changing color. The color observed may vary depending on the concentration of albumin in the sample. This variable color change is used to quantify the albumin in the sample. Test papers of the above-type require a minimum of training to use correctly. These test strips provide an accurate, convenient, and rapid vehicle for the on-the-spot determination of protein. Test papers such as these are widely used by technicians in clinical laboratories, as well as by physicians in their offices.

In more detail, these test strips include an absorbent carrier strip, i.e., paper, impregnated with a buffer, a polymer/surfactant (required for stability, wettability or to prevent leaching of the buffer) and a protein error indicator. Substantially all protein error indicators used in commercial dry phase tests are triphenylmethane derivatives sharing the basic structures below:

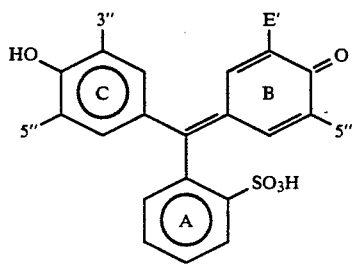

A

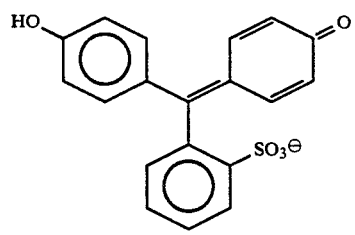

B

Structure A represents the general structure of triphenylmethane derivatives in protic solvents (water, alcohols, etc.) while structure B represents the form that predominates in the dry state or in aprotic solvents (ethers, acetonitrile, etc). Generally, triphenylmethane derived protein error indicators (phenolsulfonephthaleins) are represented as structure B. For purposes of consistency the protein error indicators of the present invention will be represented using structure B. It should be understood, however, that the protein error indicators of the present invention can also exist as structure A.

Protein error indicators are pH indicators including an ionizable group which has a pKa value that is displaced by the presence of protein. In the case of phenolsulfonephthaleins, the ionizable group is the C ring phenolic hydroxyl. The pKa value of a phenolsulfonephthalein indicator is the pH value at which one-half of the number of indicator molecules include deprotonated C ring phenolic hydroxy groups.

With regard to the phenolsulfonephthalein protein error indicators illustrated above, two deprotonation events occur in order to cause an observable color change. The first deprotonation removes the proton from the aryl sulfonic acid to yield the compound illustrated below:

The pKa of this proton is less than one. Thus, this moiety is ionized at all useful pH values. This ionized group is also responsible for the aqueous solubility of these compounds.

The second deprotonation involves releasing a proton from the C ring phenolic hydroxyl to yield the dianion below:

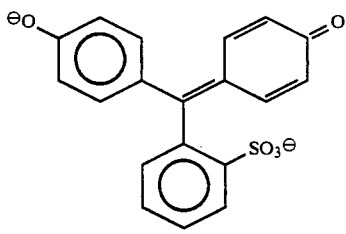

In protein error indicators, the second deprotonation causes the observable color change which is indicative of protein in the sample being tested.

The buffer provides the indicator an environment of constant pH in which to function. Thus, when the test strip is dipped into a biological fluid, which often has a significantly different pH value from the buffered environment, the indicator is not influenced by the pH of the biological fluid. This ensures that any subsequent color change in the indicator is a result of a shift in the indicator's pKa value and not a result of the pH of the sample being tested.

Test strips which are generally considered useful for the analytical determination of protein in a biological sample are described in U.S. Pat. Nos. 2,986,453, 3,095,277, 3,485,587 and 4,013,416. The test strips described therein include an absorbent carrier impregnated with a water immiscible polypropylene glycol, a buffer, and a pH indicator of the octahalosulfophthalein group. The octahalosulfophthalein indicators are triphenylmethane derivatives halogenated at the 3', 3", 5', 5", 3, 4, 5, and 6 positions. According to the patent, test strips including octahalosulfo-phthalein and water immiscible polypropylene glycols are disturbed less by interfering nitrogen-containing compounds in the test sample than test strips including other phenolsulfonephthalein indicators and surface active agents.

Although the test strips described above are less disturbed by nitrogen-containing compounds in the sample, they and other presently available test strips suffer from several common serious disadvantages. Presently available test strips have strong background negative coloration. For example, the indicators of the octahalosulfophthalein group are yellow colored in the absence of albumin. Subsequently, when albumin is added to the sample, the color changes from yellow to yellow-green to green, depending on the concentration of albumin in the sample. This background coloration is especially troublesome when it is considered that the biological fluid most often tested is urine which is normally colored yellow. Thus, small changes in the color of the test strip caused by trace amounts of albumin, i.e., from about 10 to 30 mg/dl (milligrams per deciliter) in urine could easily be masked by the color of the sample itself and go undetected. This problem is further compounded since these test strips are used by minimally trained technicians who may experience increased difficulty in interpreting the observed results. Because medical treatment is often initiated based on the results of these tests, the accurate interpretation of the results is imperative. Further, presently available test strips are not sensitive enough to detect very low levels of protein. Urinary albumin levels of from about 3 to about 10 mg/dl are significant in diagnosing several life threatening pathologies, such as diabetes and kidney disease. Nevertheless, test strips presently available cannot always accurately detect albumin below about 10 to 15 mg/dl.

Accordingly, to overcome the shortcomings discussed above, it would be extremely advantageous to provide a protein error indicator which changes from no color (colorless) to color in the presence of albumin. It would be even more advantageous if the protein error indicator accurately and clearly indicated whether albumin was present at concentrations below those presently detectable. A still further advantage would be realized by providing a test strip including such a protein error indicator.

SUMMARY OF THE INVENTION

The present invention provides the abovedescribed advantages by providing the protein error indicator compound:

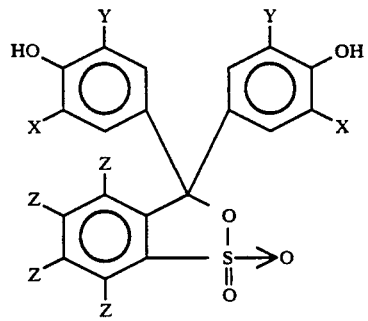

wherein:
—X is —Cl or —I where Y is —NO$_2$ and X —Cl, —Br or —I where Y is —NO;
Y is —NO$_2$ or —NO; and
Z is —Cl, Br, or —I. In accordance with one embodiment of the invention X is —I, or Br; Y is —NO$_2$; and Z is —Br, or —Cl.

In accordance with a further aspect of the present invention a protein error indicator compound is provided which has the following formula:

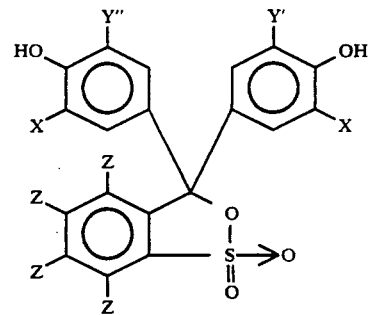

X is —Cl, —Br, —I;
Y' is —NO$_2$ or —NO;
Y" is —Cl, —Br, —I; and
Z is —Cl, —Br, —I. In accordance with one preferred embodiment, X is —I; Y' is —NO$_2$; Y" is Br; and Z is —Br.

A still further aspect of the present invention is directed to an analytical test strip for the detection of protein in a biological sample comprising an absorbent carrier impregnated with one of the protein error indicator compounds described above.

Another aspect of the present invention is directed to a method for the detection of protein in a biological sample, the method comprising the step of wetting an analytical test strip with the biological sample. The test strip includes an absorbent carrier impregnated with one of the protein error indicator compounds described above. The test strip is then observed to detect any color change. A color change is indicative of protein in the biological sample.

DESCRIPTION OF THE PREFERRED EMBODIMENTS

Figure 1:
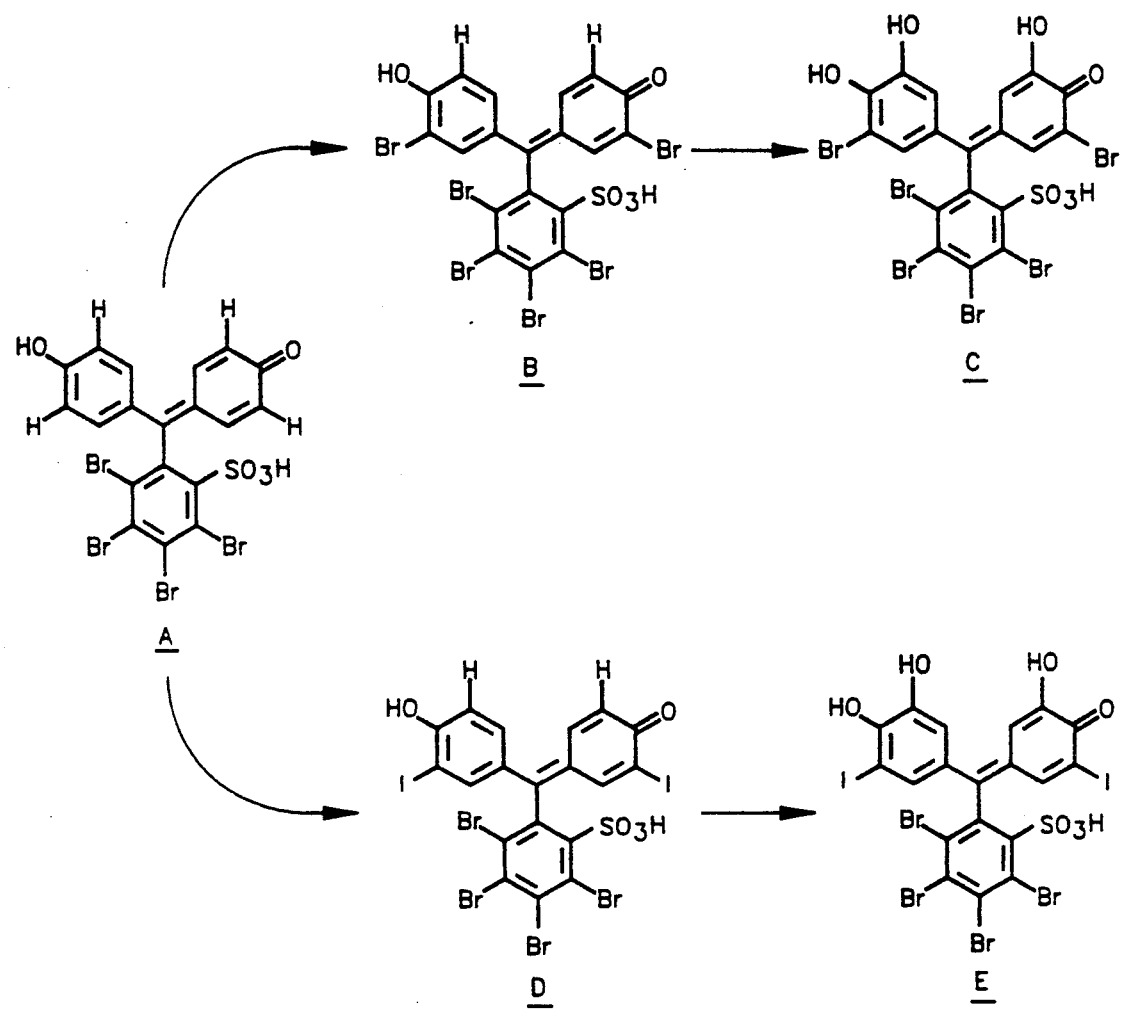
FIG. 1 is a schematic of processes for the synthesis of nitroso substituted protein error indicators.

In accordance with the invention, it has been discovered that test strips for the determination of protein in biological fluids having a significantly increased sensitivity to protein can be obtained by impregnating an absorbent paper test strip with the novel protein error indicators of the present invention.

Test strips including the below-described novel protein error indicators are light gray or colorless, and on immersion into a biological sample containing protein become strongly colored blue, the intensity of the color reflecting the concentration of protein in the sample. The blue color produced is clearly distinct from the light gray or no color of a negative test.

With reference to the observable color change from light gray or no color to blue, tests strips prepared in accordance with the present invention provide an improved diagnostic aid for the detection of protein in biological fluids by "producing" color in the presence of protein. This is distinguishable from other test strips which "change" color in the presence of albumin. The characteristic of light gray or no color for a negative test, and color in a positive test is seen as a significant departure from previous methods and indicators used to detect protein in biological samples. More specifically, the invention provides clinicians with a simple, reliable and accurate method for detecting protein in biological samples. The change from light gray or no color to a blue color makes analytical test strips including these protein error indicators easy to read. This will result in less misdiagnosis, and accordingly, lower costs for the patient and health care provider.

Further, test strips prepared in accordance with the present invention positively detect a range of from about 2 to about 500 mg/dl of protein in a sample. Prior to the present invention, albumin concentrations of less than about 10 mg/dl were not accurately detectable. The detection of protein at these very low concentrations using the present invention makes possible the early diagnosis of several life threatening pathologies, including diabetes and kidney disease. For example, the detection of albuminuria at levels at or above 3 mg/dl will help clinicians to better diagnose diabetes in its early stages. In light of this significant advancement in the diagnosis of disease obtained with the present invention, the protein error indicators and test strips of the present invention provide a significant advancement in the art.

The present invention achieves the abovedescribed significant advantages by providing a novel group of protein error indicators including nitro or nitroso substituent groups in the B and C rings of a partially halogenated triphenylmethane compound. In more detail, in accordance with one embodiment of the invention, the protein error indicator of the present invention is the compound:

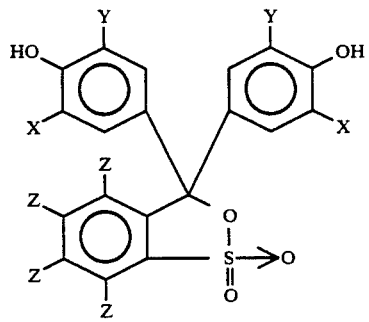

wherein:

X is —Cl or —I where Y is —NO$_2$ and X is —Cl, —Br or —I where Y is —NO.

Y is —NO$_2$ or —NO; and Z is —Cl, —Br, —I. Preferably, X is —I, or —Br; Y is —NO$_2$; and Z is —Br, or —Cl. More preferably, X is —I; Y is —NO$_2$; and Z is —Br.

In accordance with a further embodiment of the present invention, a protein error indicator compound is provided which has the following formula:

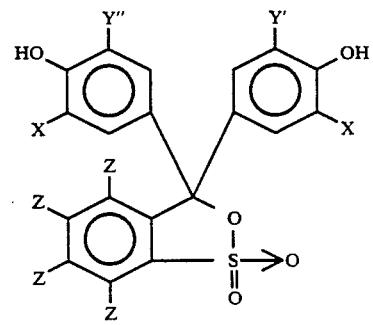

wherein: X is —Cl, —Br, or —I; Y' is —NO$_2$ or —NO; Y" is —Cl, —Br, or —I; and Z is —Cl, —Br, or —I.

More preferably, X is —I; Y' is —NO₂; Y" is —Br; and Z is —Br.

Referring to the figures, FIG. 1 generally illustrates the synthesis of two dinitrososubstituted indicators of the present invention. More specifically, FIG. 1 shows possible synthesis protocols for 3', 3"-dinitroso5', 5", 3,4,5,6-hexabromophenolsulfonephthalein (compound C of FIG. 1) and 3', 3"-dinitroso-5', 5"-diiodo-3,4,5,6-tetrabromophenolsulfonephthalein (compound E of FIG. 1) from the commercially available 3,4,5,6-tetrabromophenolsulfonephthalein (compound A of FIG. 1). The dibromo-intermediate (compound B of FIG. 1) is readily prepared by treating a solution of tetrabromophenolsulfonephthalein in acetic acid (HOAc) with two equivalents of molecular bromine at ambient temperature. This is then nitrosylated in acetonitrile (CH₃CN) by an acid catalyzed reaction with isoamyl nitrite to afford 3', 3"-dinitroso-5', 541 , 3,4,5,6-hexabromophenolsulfonephthalein.

The diiodo-analogs are prepared similarly. 3,4,5,6-tetrabromoohenolsulfonephthalein is iodinated by reaction with 3.0 equivalents of iodine monochloride (ICl) in HOAc at ambient temperature to give the compound illustrated as compound D in FIG. 1. This compound is then nitrosylated as above to afford 3', 3"-dinitroso-5',5"-diiodo-3,4,5,6-tetrabromophenolsulfonephthalein. Following the above-described protocol, the synthesis of analogs including other halogens, alkyl groups or protons (H) at the positions 3', 3", 3,4,5,5', 5" or 6 is straightforward and yield the anticipated compounds.

Figure 2:
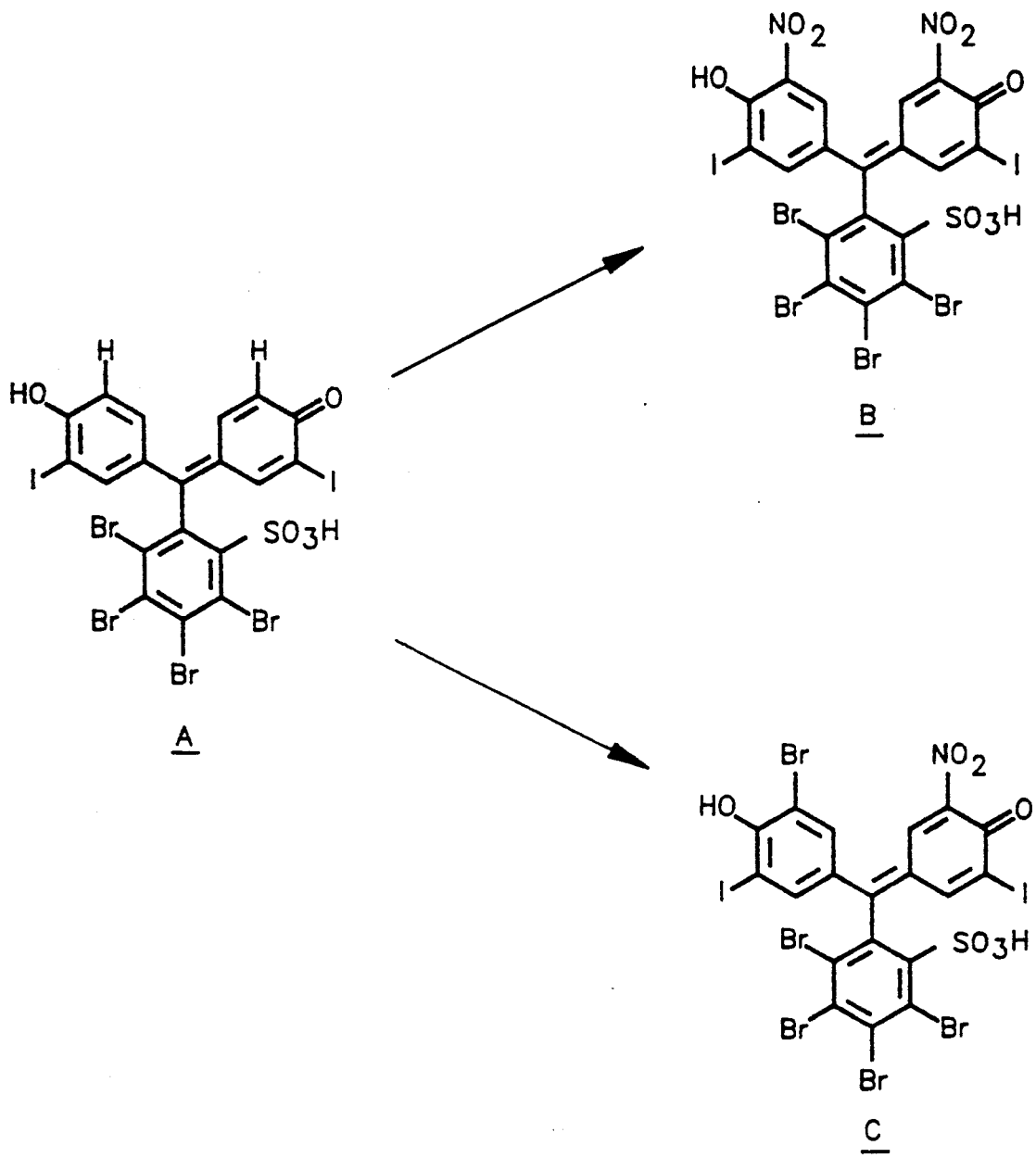
FIG. 2 is a schematic of processes for the synthesis of nitro substituted protein error indicators.

FIG. 2 generally illustrates the synthesis of the nitro-substituted protein error indicators of the present invention. Treatment of a solution of compound A of FIG. 2 in HOAc with no more than two equivalents of nitric acid (HNO₃) at ambient temperature affords 3', 3"-dinitro-5', 5"-diiodo-3,4,5,6-tetrabromophenolsulfonephthalein (compound B of FIG. 2). Slow treatment of compound A of FIG. 2 with one equivalent of HNO₃ in HOAc at ambient temperature followed by treatment with excess Br₂ at reflux gives the mononitro-analog 3"-nitro-5', 5"-diiodo-3,3',4,5,6-pentabromophenolsulfonephthalein (compound C of FIG. 2). Following the above-described protocol, the synthesis of analogs including other halogens, alkyl groups or protons (H) at the positions 3', 3", 3,4,5,5', 5" or 6 is straightforward and yield the anticipated compounds. Described below in the Examples are detailed synthesis protocols for preparing each of the compounds illustrated in FIGS. 1 and 2.

Without limiting the invention, it is believed that the substitution of nitro or nitroso group(s) in the B and C rings is responsible for the increased sensitivity of these compounds to urinary albumin and the surprising characteristic of changing from light gray or no color to blue in the presence of very low concentrations of protein. It is believed that the phenomena of electron withdrawal and charge dispersal combine to provide indicators of increased sensitivity.

In more detail, it is believed that the highly electronegative nitro and nitroso groups, situated adjacent to the hydroxy groups at the 4' and 4" positions, increase the reactivity of those hydroxy groups. In addition, it is also believed that the reactivity of the hydroxy groups is further enhanced through resonance stability. It is believed that ionic forms of the molecule are stabilized through charge dispersal. The resonance stability imparted by the substituent nitro and nitroso groups increases the acidity of the adjacent hydroxy hydrogen at the 4' and 4" positions. These phenomena combine, synergistically it is believed, to reduce the pKa of the indicators, and accordingly, increase the sensitivity of the indicator to albumin.

A further aspect of the present invention is directed to an analytical test strip for the detection of protein in a biological sample comprising an absorbent carrier impregnated with one of the inventive protein error indicator compounds described above. The absorbent matrix material of the test strip is preferably a filter paper. Other materials useful as the absorbent matrix material include felt, porous ceramic strips, porous synthetic membranes, and woven or matted glass fibers described in U.S. Pat. No. 3,846,247. Also suggested are the use of wood, cloth, sponge material and argillaceous substances described in U.S. Pat. No. 3,552,928). Alternatively, the carrier matrix can be non-porous, such as various polymeric films, glass and the like. All such carrier matrix materials are feasible for use in the present invention, as are others. It has been found that filter paper is especially suitable.

The absorbent strip is preferably impregnated with a buffer. Any buffer system which can be adjusted to a pH of from about 1.5 to about 4.5 is useful in the practice of the present invention. Preferably, the buffer system is adjusted to a pH of from about 2.0 to about 3.0, and most preferably about 2.5.

The test strip can also be impregnated with a color enhancing polymer. For purposes of the present invention the term "color enhavning polymer" it is intended to mean a polymer having a molecular weight from about 400 to about 25,000 which increases both the kinetics of the color formation and the dose response of the protein error indicators of the invention or reduces the back ground color of a negative test. Preferred color enhancing polymers include polypropylene glycols, polycarbonates and polyvinylethers. Both water miscible and immiscible polypropylene glycols are useful in the practice of the present invention. It is preferred that the polypropylene glycol has a molecular weight of from about 400 to about 10,000. More preferably, the polypropylene glycol has a molecular weight of from about 1,000 to about 4,000. Most preferably, however, the polypropylene glycol has a molecular weight of about 2,000. Water immiscible polypropylene glycols useful in the practice of the present invention are discussed in detail in U.S. Pat. No. 4,013,416. Nevertheless, it has been determined that water miscible polypropylene glycols having an average molecular weight of about 400 are useful in the practice of the present invention. Other preferred color enhancing polymers include: a polycarbonate available under the tradename designation of KOK 10,002 from Bayer AG, Germany; a polypropylene oxide and ethylene oxide adduct of 1,6-dimethyl-4-nonyl-phenol available under the tradename designation of Fenoil D4030 from Bayer AG, Germany; a polyvinylether available under the tradename designation Lutonal I30 from BASF, US; and a polymer available under the tradename designation Baylube FE3016 from Bayer AG, Germany.

It has been determined that test strips of the present invention which include certain color enhancing polymers i.e., polypropylene glycols, have an increased dose response range. Polypropylene glycols also improved the kinetics for the albumin response throughout the entire dose response range for the test strip. As a result, test strips including the inventive indicators and a polypropylene glycol develop more color at a much faster rate than without the color enhancing polymer. Also, tests of the invention demonstrate that test strips including certain color enhancing polymers, i.e., KOK 10,002, and polypropylene glycols, produce better resolution between albumin levels. The data shown below in the Examples demonstrate that the preferred color enhancing polymers of the present invention, can in some instances, increase the pKa of the indicator, the resolution and the albumin dose response, and the kinetics of color development.

The following Examples are presented to describe preferred embodiments and utilities of the present invention and are not meant to limit the present invention unless otherwise stated in the claims appended hereto.

EXAMPLES

Example 1. 3', 3", 3,4,5,6-Hexabromophenolsulfonephthalein

A solution of 3,4,5,6-tetrabromophenolsulfonephthalein, obtained from the Aldrich Chemical Co., Milwaukee, WI USA, [5.03 g (grams), 7.5 mmole (millimoles)] in acetic acid [(HOAc), 50 ml (milliliters)] was maintained at ambient temperature under an inert gas atmosphere. The solution was dropwise treated for 10 minutes with a solution of bromine, obtained from the Aldrich Chemical Company, (2.4 g, 15 mmole, in HOAc, 10 ml), and thereafter stirred overnight. The solids that separated from the reaction mixture were collected by filtration, washed with HOAc and dried in vacuo to afford 3', 3", 3,4,5,6-hexabromophenolsulfonephthalein. Recrystallization from boiling HOAc afforded the analytically pure compound (1.93 g, 29.3%) as a pale pink powder which softened at 159–160° C., melted with gas evolution at 162–164° C. and then resolidified with no melting point below 270° C. Spectroscopic data identifying the compound are set forth below in Table 1.

TABLE 1

| IR (KBr) cm$^{-1}$ | 3435, 1703, 1605, 1497, 1416, 1360, 1340, 1295, 1227, 1192 |
|---|---|
| $^1$H NMR (DMSO-d$^6$)δ | 8.03(s, 2H), 7.59(d, J=2.4Hz, 2H), 7.31(d of d, J$_1$=8.7Hz and J$_2$=2.4 Hz, 2H), 7.11(d, J=8.7 Hz, 2H) |
| Analysis calculated for C$_{19}$H$_8$Br$_6$O$_5$S.HOAc: | C, 28.90; H, 1.39 |
| Found: | C, 28.55; H, 1.38. |

Example 2. 5', 5"-dinitroso-3', 3", 3,4,5,6-hexabromophenolsulfonephthalein

A stirred solution of 3', 3",3,4,5,6-hexabromophenolsulfonephthalein (0.67 g, 0.8 mmole) in anhydrous acetonitrile (CH$_3$CN, 50 ml) was maintained at an ambient temperature under an inert gas atmosphere. The solution was treated with a catalytic amount of HOAc (one drop) and isoamyl nitrite (0.56 g, 4.8 mmole), and thereafter stirred for 4 days. The solids that separated from the reaction mixture were collected by filtration, and washed with CH$_3$CN (10 ml). The solid was dried in vacuo to afford 5', 5"-dinitroso-3', 3", 3,4,5,6-hexabromophenolsulfonephthalein (0.45 g, 64%) as an analytically pure yellow powder with a melting point of 267–269° C. A second crop was subsequently obtained from the concentrated mother liquors (0.03 g; 4%). Spectroscopic data identifying the compound are set forth below in Table 2.

TABLE 2

| IR (KBr) cm$^{-1}$ | 1621, 1543, 1468, 1416, 1361, 1341, 1325, 1258, 1194, 1162, 1096 |
|---|---|
| $^1$H NMR (DMSO-d$^6$)δ | 7.93(d, J=2.5Hz, 2H), 7.73(d, J=2.5Hz, 2H), 4.20 (v. br. s, 2H) |
| Analysis calculated for C$_{19}$H$_6$Br$_6$N$_2$O$_7$S: | C, 25.76; H, 0.68; N, 3.16 |
| Found: | C, 25.61; H, 0.58; N, 3.40. |

Example 3. 3", 3"-diiodo-3,4,5,6-tetrabromophenolsulfonephthalein 3,4,5,6-tetrabromophenolsulfonephthalein (20.1 g, 30 mmole) was dissolved in 70° C. HOAc (550 ml) then cooled to ambient temperature in a water bath. The stirred solution was maintained under an inert gas atmosphere. The solution was treated with a solution of iodine monochloride (ICl) (14.61 g, 90 mmole) in HOAc (50 ml) and left at ambient temperature for 22.3 hours. The reaction mixture was filtered through a pad of Celite 521 (Johns-Manville Corp., Denver, Co., USA), and evaporated to dryness in vacuo. The resulting red tar was taken up in HOAc (150 ml). The solids which separated from this solution on standing were filtered, washed with HOAc and dried in vacuo to afford 3', 3"-diiodo-3,4,5,6-tetrabromophenolsulfonephthalein (9.66 g, 34.9%) as a pink powder. A second crop was subsequently obtained from the concentrated mother liquors (4.03 g , 14.6%). Spectroscopic data identifying the compound are set forth below in Table 3.

TABLE 3

| IR (KBr) cm$^{-1}$ | 1697, 1598, 1486, 1405, 1338, 1293, 1226, 1191 |
|---|---|
| $^1$H NMR (DMF-d$^7$)δ | 8.03(s, 2H), 7.97(d, J=2.3Hz, 2H), 7.49(d of d, J$_1$=8.6Hz and J$_2$=2.3Hz, 2H), 7.02(d, J=8.6Hz, 2H) |
| Analysis calculated for C$_{19}$H$_8$Br$_4$I$_2$O$_5$S.HOAc: | C, 25.69; H, 1.23 |
| Found: | C, 25.94; H, 0.94. |

Example 4. 5', 5"-dinitroso-3', 3"-diiodo-3,4,5,6-tetrabromoohenolsulfoneohthalein A solution of 3', 3"-diiodo-3,4,5,6-tetrabromophenolsulfonephthalein (1.47 g, 1.6 mmole) in anhydrous CH$_3$CN (50 ml) was maintained at ambient temperature under an inert gas atmosphere. The mixture was thereafter treated with a catalytic amount of HOAc (2 drops) and isoamyl nitrite (2.3 g, 20 mmole). The resulting mixture was allowed to stir for two days. The solids that separated from the reaction mixture were collected by filtration, washed with cold CH$_3$CN and dried in vacuo to give the compound 5', 5"-dinitroso-3', 3"-diiodo-3,4,5,6-tetrabromophenolsulfonephthalein (0.41g, 26%). Recrystallization from CH$_3$CN (150 ml) afforded the analytical sample as a pale yellow wool with no melting point below 270° C. I5 Spectroscopic data identifying the compound are set forth below in Table 4.

TABLE 4

| IR (KBr) cm$^{-1}$ | 1616, 1541, 1460, 1410, 1360, 1322, 1257, 1195, 1091 |
|---|---|
| $^1$H NMR (DMSO-d$^6$)δ | 8.00(d of d, J$_1$=2.0Hz and |

| | |
|---|---|
| | $J_2=1.2$Hz, 2H), 7.93(d, $J=2.2$Hz, 2H), 4.76(v. br. s, 2H) |
| Analysis calculated for $C_{19}H_6Br_4I_2N_2O_7S$: | |
| | C, 22.93; H, 0.46; N, 2.80 |
| Found: | C, 23.08; H, 0.71; N, 2.83. |

Example 5. 5', 5''-dinitro-3', 3''-diiodo-3,4,5,6-tetrabromophenolsulfonephthalein(-DIDNTB)

A stirred solution 3', 3''-diiodo-3,4,5,6-tetrabromophenolsulfonephthalein (1.85 g, 2.0 mmole) in boiling HOAc (90 ml) was cooled to about 16-20° C. The solution was dropwise treated, over four minutes, with a solution of 90% nitric acid (0.28 g, 4.0 mmole) in HOAc (10 ml) and left to stir overnight at ambient temperature under an inert gas atmosphere. The solids that separated from the reaction mixture were collected by filtration, washed with HOAc (5 ml) and dried in vacuo to afford a crude preparation of 5', 5''-dinitro-3', 3''-diiodo-3,4,5,6-tetrabromophenolsulfonephthalein. One recrystallization from HOAc (110 ml) afforded the analytically pure compound 5', 5''-dinitro-3', 3''-diiodo-3,4,5,6-tetrabromophenolsulfonephthalein (0.90 g, 38%) as a yellow powder. This material had no distinct melting point. However, the material shrunk at about 189-190° C., evolved gas at about 210-220° C. and melted at about 225° C. Spectroscopic data identifying the compound are set forth below in Table 5.

TABLE 5

| | |
|---|---|
| IR (KBr) cm$^{-1}$ | 1707, 1616, 1541, 1460, 1408, 1370, 1322, 1257, 1195, 1092 |
| $^1$H NMR (DMSO-d$^6$)δ | 8.03(d, $J=2.4$Hz, 2H), 7.91(d, $J=2.4$Hz, 2H), 6.0–7.0(br. s, 2H) |
| Analysis calculated for $C_{19}H_6N_2Br_4I_2O_9S\cdot 2HOAc$: | |
| | C, 24.40; H, 1.25; N, 2.48 |
| Found: | C, 24.49; H, 1.00; N, 2.42. |

Example 6. 5'-nitro-3', 3''-diiodo-5'', 3,4,5,6-pentabromophenolsulfonephthalein A stirred solution of 3', 3''-diiodo-3,4,5,6-tetrabromophenolsulfonephthalein (0.92 g, 1.0 mmole) in boiling HOAc was cooled to ambient temperature, and maintained under an inert gas atmosphere. The solution was slowly treated dropwise, over 1.5 hours, with 1M HNO$_3$ in HOAc (1.05 ml; 1.05 mmole). Once the addition was complete, the reaction mixture was allowed to stir for five minutes. Thereafter the reaction mixture was treated with a solution of Br$_2$ in HOAc (1.5 ml, 1.5 mmole) and refluxed for 5.5 hours. The mixture was thereafter cooled to ambient temperature and evaporated to dryness in vacuo to afford a golden-brown glass (1.10 g). The crude product was taken up in a minimum volume of ethyl acetate (EtOAc) and diluted with HOAc to afford a crystalline solid. After two recrystallizations there was obtained analytically pure 5'-nitro-3', 3''-diiodo-5'', 3,4,5,6-pentabromophenolsulfonephthalein (0.57 g, 54.5%) as a bright yellow powder. Spectroscopic data identifying the compound are set forth below in Table 6.

TABLE 6

| | |
|---|---|
| IR (KBr) cm$^{-1}$ | 1708, 1614, 1540, 1462, 1406, 1371, 1338, 1324, 1252, 1194, 1162, 1091, 1016, 823, 789, 765, 723, 671 |
| $^1$H NMR (DMSO-d$^6$)δ | 8.03(d of d, $J_1=24.8$Hz and $J_2=2.3$Hz, 2H), 7.98(d of d, $J_1=22.7$Hz, and $J_2=2.4$ Hz, 1H), 7.90(br. m, 1H), 7.67(br. m, 1H) |
| Analysis Calculated for $C_{19}H_6Br_4I_2NO_7S$: | |
| | C, 21.82; H, 0.58; N, 1.34 |
| Found: | C, 22.16; H, 0.33; N, 1.33 |

Example 7. pKa Titration of Indicator

The pKa of the indicator was obtained by titrating E & D 237 (Ahlstrom Filtration, Inc., Mount Holley Springs, PA, USA) filter paper strips containing the dye DIDNTB with buffers of varying pH. Two trials were conducted. In one trial, the test strip additionally included the protein enhancing polymer polypropylene glycol (PPG) having a molecular weight of about 2000. In the strip including PPG, the ratio of the protonated to the deprotonated species was increased. This was expressed as a reduction in the bleak K/S value for the strip including PPG All strips were light gray or off-white in the absence of protein, and in the presence of protein turned blue.

Formation of the blue species was followed at 610 nm and is expressed in K/S units. K/S units were calculated from the formula:

$$K/S = \frac{(1-R)^2}{2R}$$

wherein R is the fraction of reflectance from the test device, K is a constant, and S is the light scattering coefficient of the particular reflecting medium. The above equation is a simplified form of the well-known Kubelka-Munk equation (See Gustav Kortum, "Reflectance Spectroscopy," pp. 106–11, Springer Verlas, New York (1969).

Figure 3:
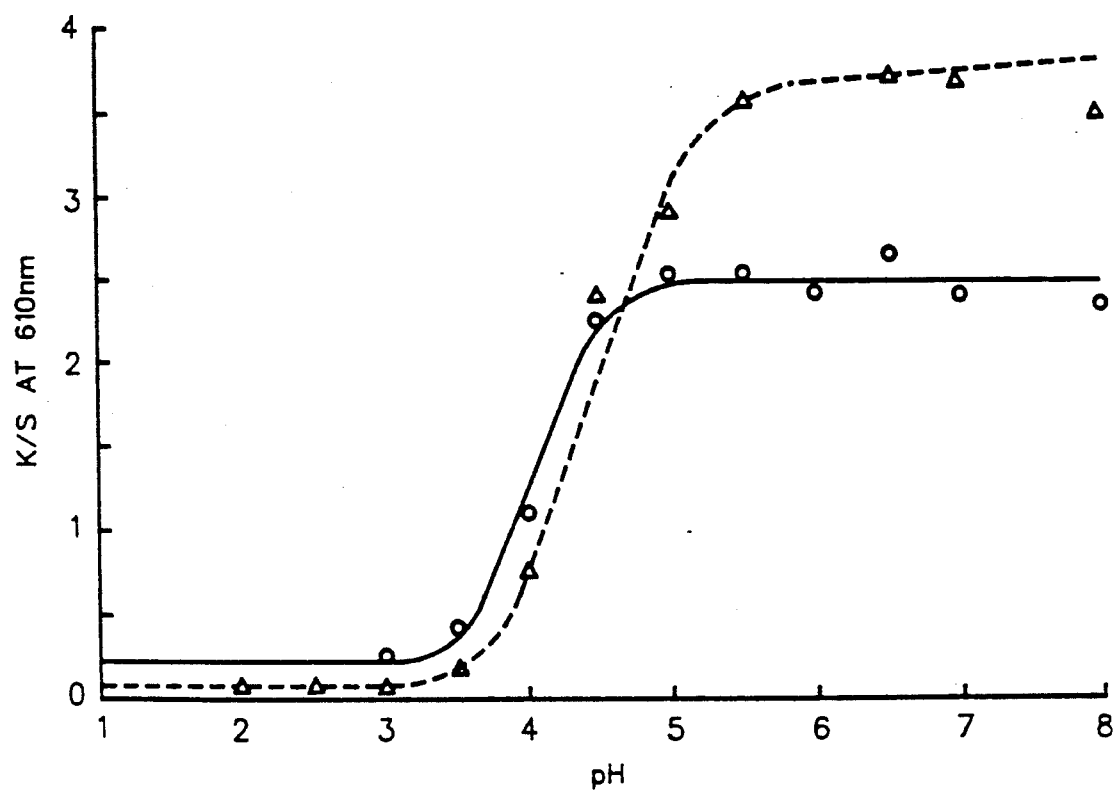
FIG. 3 illustrates the titration curves for analytical test strips impregnated with DIDNTB (5', 5"-dinitro-3', 3"-diiodo-3,4,5,6-tetrabromophenolsulfonephthalein) alone (—O—), and with a polypropylene glycol having a molecule weight of 2000 (—△—)

Referring to FIG. 3, the low and high plateaus in the titration curves indicate at which pH values the protonated and deprotonated forms of 5', 5''-dinitro-3', 3''-diiodo-3,4,5,6-tetrabromophenolsulfonephthalein (DIDNTB) occurred. In both trials the C ring hydroxy group of DIDNTB was fully protonated at pH <2.5 (K/S was at a minimum) and fully deprotonated at pH ≧5 (maximum K/S). The K/S values were determined at 25 seconds.

In the presence of a polypropylene glycol (PPG) having a molecular weight of about 2000, the pKa of DIDNTB was increased from 4.06 to 4.47. This parameter was believed to be only an apparent quantity, since it also contained the effect of the paper matrix. In fact, the solution pKa of DIDNTB was 2.9. In light of the determined titration parameters, the pKa of the indicator is believed to be influenced by both the paper matrix and the color enhancing polymer.

At the pH value one unit below the pKa, the color of the indicator DIDNTB was reduced by the polypropylene glycol from a light gray to no color. Further, in the test strip including polypropylene glycol the K/S of the deprotonated peak was increased from 2.5 to 3.9, corresponding to a 56% enhancement in the apparent extinction coefficient. This was reflected as more color being generated by the indicator in the presence of protein.

Example 8. Dose Response with a Biological Fluid

Figure 4:
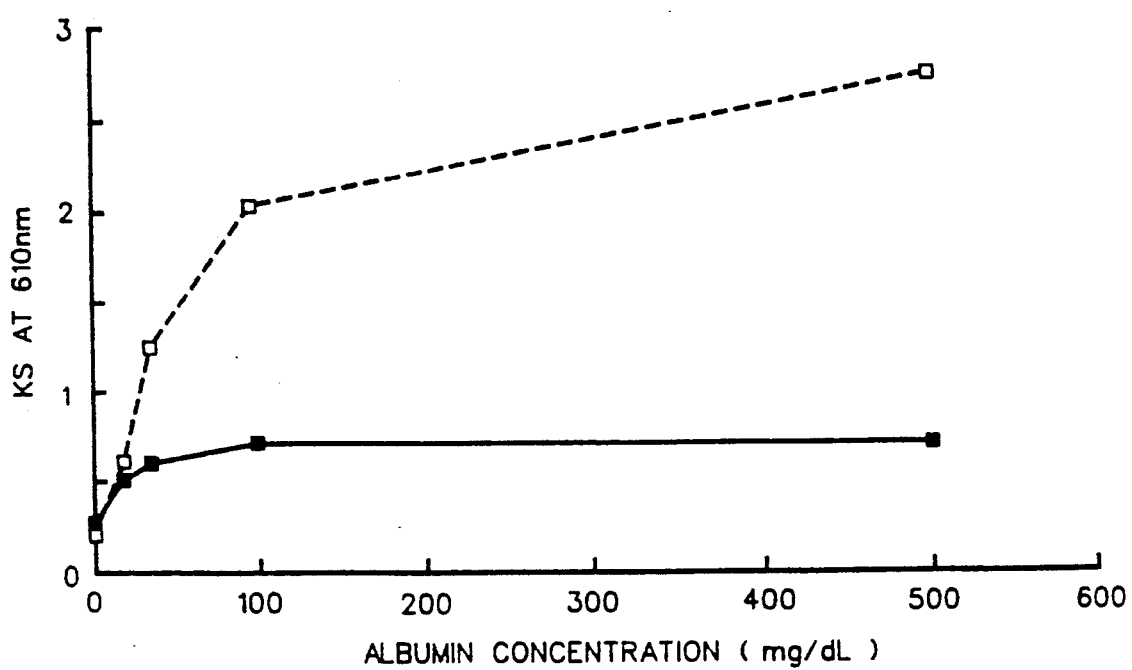
FIG. 4 illustrates the dose response curves of analytical test strips impregnated with DIDNTB alone (—■—), and with a polypropylene glycol having a molecule weight of 2000 (—□—)

A urine pool with a specific gravity of 1.007, which was shown by immunoassay to be devoid of albumin, was spiked to various clinically significant albumin levels with Pentex ® human serum albumin (Miles Inc., Elkhart, IN. These spiked urine pools were then tested with one set of indicator strips containing DIDNTB alone, and a second set of strips including DIDNTB and a polypropylene glycol having a molecular weight of about 2000, on a CLINITEK ® 200 instrument (Miles Inc., Elkhart, IN. The data is summarized in FIG. 4. The strip pH was 2.5, 1.6 units below the pKa of DIDNTB. The strip pH is that pH value at which there is minimal background color with maximal sensitivity. The K/S was determined at 25 seconds.

Resolution was quantitatively expressed in delta K/S between albumin levels, as shown below in Table 7.

TABLE 7

| FORMULATION | K/S@ NEGATIVE LEVEL | K/S BETWEEN ALBUMIN LEVELS (mg/dl) with standard deviation in parenthesis (n = 5) | | | |
|---|---|---|---|---|---|
| | | 0–15 | 15–30 | 30–100 | 100–500 |
| DIDNTB | 0.216 | 0.282 (0.02) | 0.079 (0.03) | 0.102 (0.03) | 0.048 (0.03) |
| DIDNTB/PPG | 0.153 | 0.468 (0.02) | 0.593 (0.06) | 0.894 (0.14) | 0.587 (0.16) |

Both test strips clearly indicated by color production the presence of albumin at concentrations of 15 mg/dl. In fact, the strip including only DIDNTB was more sensitive to protein concentrations below 30 mg/dl than it was to higher concentrations. This is a level below which most commercial test strips have poor resolution. On the other hand, the strip including polypropylene glycol was sensitive to protein up to a concentration of 500 mg/dl. Thus, an increase in resolution was produced by the polypropylene glycol. Furthermore, the background color was reduced at the negative level from slightly gray to colorless or off-white, as denoted by a decrease in the K/S value of the strip.

Example 9. Kinetic Measurements

Figure 5A:
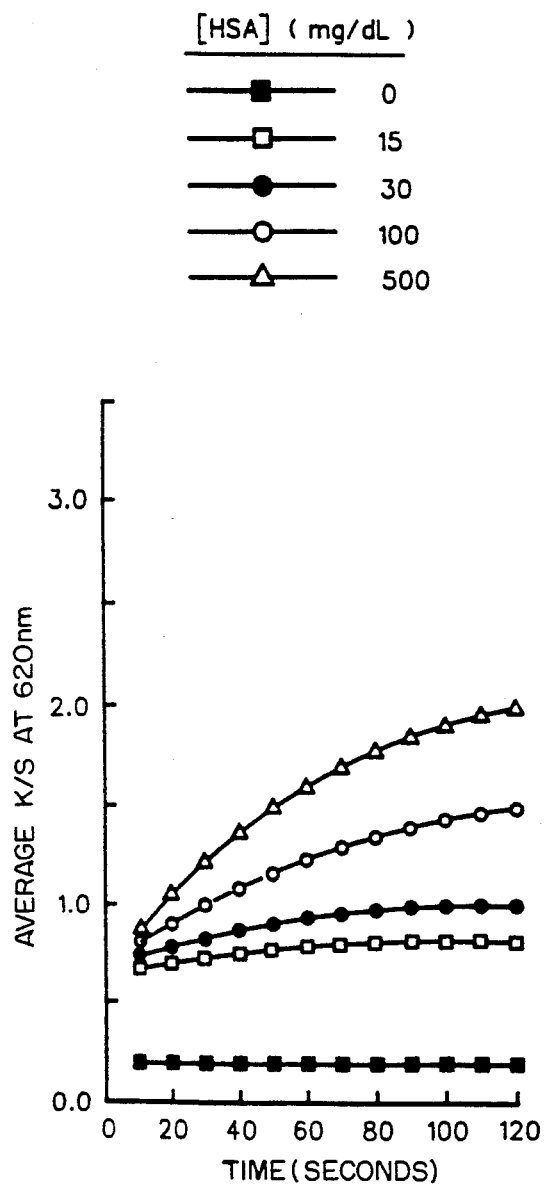
FIG. 5 illustrates the kinetic response curves of analytical test strips impregnated with DIDNTB alone (—A—), and with a polypropylene glycol having a molecular weight of 2000 (—B—)
Figure 5B:
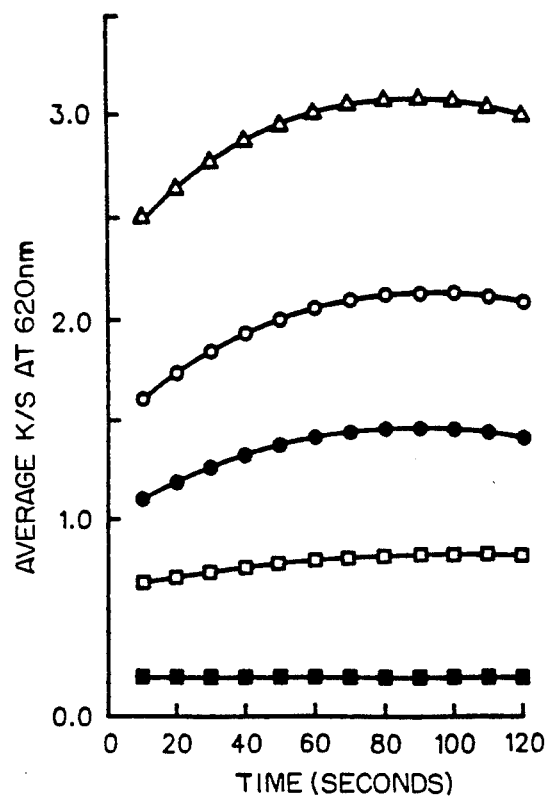

Using the same urine pool described above, kinetic measurements were made using the same test strips and a Miles rapid scanner instrument. The data is summarized in FIG. 5. FIG. 5 shows enhanced kinetics and greater resolution between albumin levels when the polypropylene glycol was used with the DIDNTB. Both test strips, however, clearly detected albumin at 15 mg/dl.

Figure 6:
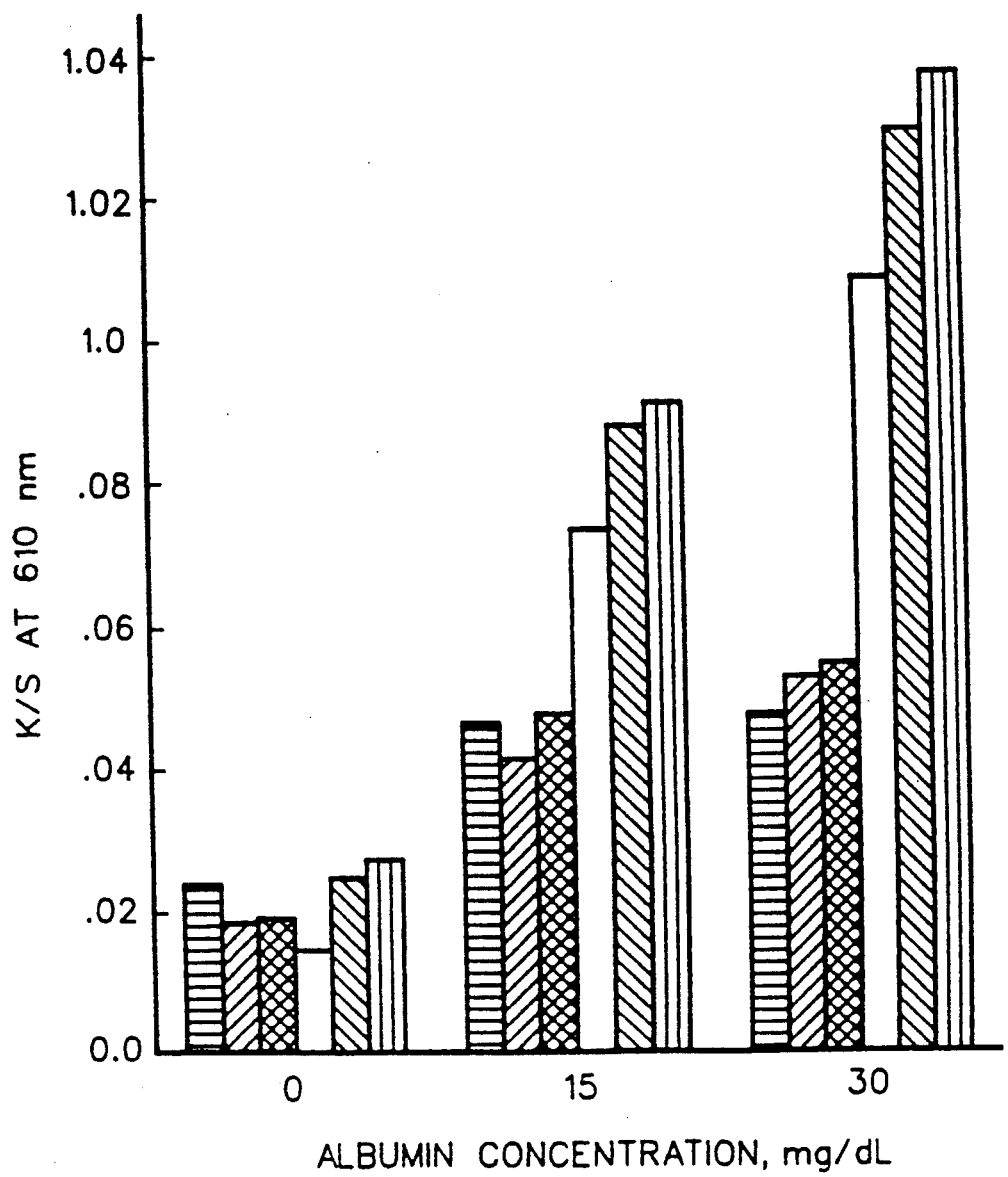
FIG. 6 is a bar graph illustrating the dose response of analytical test strips impregnated with DIDNTB alone (—■—), DIDNTB and Fenoil D4030 (—▨—), DIDNTB and Baylube FE3016 (—⊡—), DIDNTB and P-2000 (—□—), DIDNTB and KOK 10,000 (—⊞—), and DIDNTB and PPG D400 (—⊟—).

Example 10. A Comparison Of Reagent Strips Including One Of Several Selected Color Enhancing Polymers Using the same urine pool described above, measurements were made using test strips including DIDNTB, and no color enhancing polymer or one color enhancing polymer selected from the group consisting of Fenoil D4030, Baylube FE3016, KOK 10,002, P-2000 (a polypropylene glycol having an average molecule weight of 2000 and available from Fluka Chemical Company under the tradename designation P-2000), and PPG D400 (a polypropylene glycol having an average molecule weight of 400 and available from Olin Chemical Company under the tradename designation PPG D400). The K/S value was determined at 25 seconds. The data is summarized in FIG. 6.

The blank background color was slightly decreased by Fenoil D4030, Baylube FE3016, and P-2000 from slightly gray to colorless. KOK 10,002 and PPG D400 did not decrease the background color; however, they, in addition to P-2000, caused a marked enhancement in dose response. From the data summarized in FIG. 6, P-2000 would be a more preferred color enhancing polymer since it improves resolution between albumin concentrations, while at the same time reducing the background color. These same results have also been demonstrated with polypropylene glycols having molecular weights of 1000 and 4000.

Example 11. A Second Comparison Of Reagent Strips Including One Of Several Selected Color Enhancing Polymers Whatman CCP 500 paper reagent strips were impregnated with the following dip solutions and dried according to standard procedures as follows. The control reagent strip was prepared by first dipping the strip in a 0.5M citrate buffer, pH 2.5, and thereafter dipping the strip into a bath including 0.30 mM DIDNTB in tetrahydrofuran (THF). The other strips were prepared in substantially the same manner with the exception that the second bath also included 1% color-enhancing polymer. Polymers used in the example were PPG P-2000 from Fluka, various molecular weight PPG's from Olin (D series), polypropylene glycol monobutylethers (PPGMBE) from Dow Chemical, and KOK 10,002 from Bayer.

Strips prepared from the above reagent paper were tested with urine samples from a urine pool with a specific gravity of 1.007 which was shown by immunoassay to be devoid of albumin and was spiked to various clinically significant albumin levels with Pentex human serum albumin (HSA). The reflectance of the strips at 610 nm was measured at 25 seconds after dipping the strip in the test solution. The effect of the polymer on the blank can be quantitatively expressed as the K/S obtained in the absence of albumin (negative level), while the improvement in resolution as a result of the increased rate of color development can be expressed in delta K/S between albumin levels. The data is summarized in the following table.

| Formulation | K/S @ Negative Level | K/S BETWEEN ALBUMIN LEVELS standard deviation in parenthesis (n = 5) | |
|---|---|---|---|
| | | 0–15 mg/dL | 15–30 mg/dL |
| No Polymer | 0.253 (0.012) | 0.223 (0.02) | 0.027 (0.02) |
| PPG P-2000 | 0.156 (0.008) | 0.596 (0.02) | 0.360 (0.03) |
| PPG D-2000 | 0.177 (0.009) | 0.607 (0.01) | 0.457 (0.03) |
| PPG D-1200 | 0.196 (0.004) | 0.704 (0.03) | 0.524 (0.03) |
| PPG D-400 | 0.280 (0.014) | 0.644 (0.03) | 0.499 (0.07) |
| PPGMBE L910 | 0.165 (0.002) | 0.648 (0.03) | 0.480 (0.05) |
| PPGMBE L1150 | 0.151 (0.007) | 0.583 (0.02) | 0.446 (0.03) |
| KOK 10,002 | 0.251 (0.005) | 0.650 (0.05) | 0.426 (0.08) |

All of the polymers in this group produced a large increase in resolution which is represented by the enhancement in delta K/S from 2 to 20 fold over that of the no polymer control. The much smaller effect on the background is evident from the decrease in K/S at the negative level for all of the polymers except the PPG D-400 and the KOK 10,002. Therefore, the ability to produce both effects are usually, but not necessarily always, resident in the same polymer. The two PPGMBE polymers have performance characteristics which were as good or slightly better than the PPG polymers.

Example 12. Reagent Strip Preparation

One method for the preparation of the urinary protein reagent strip discussed herein is shown below. The method described is a continuous method for mass producing urinary protein reagent test strips.

According to the method, a thin absorbent strip of paper is moved through the line at a preferred speed of about four feet per minute. One preferred paper being E & D 237. If a color enhancing polymer, such as polypropylene glycol, is to be incorporated into the test strip, the paper is first dipped into a bath including the color enhancing polymer dissolved in ethanol or another suitable organic solvent. For example, if a polypropylene glycol is used, the ethanol bath should include one percent polypropylene glycol. A preferred polypropylene glycol having a molecular average weight of about 2000 is available from Fluka Chemical Company under the tradename designation P-2000. If, however, a test paper is being manufactured which does not include a color enhancing polymer, the first dip should be in only ethanol. The paper is subsequently dipped a second time in a bath containing the protein error indicator, and a buffer dissolved in an aqueous-ethanol mixture or another suitable organic solvent. According to one preferred method, the second bath contains 0.025% DIDNTB and 0.45 molar potassium citrate buffer at a pH of 2.5 in 50% ethanol. The test strip is then passed through a dryer having an air pressure of one inch of water and a temperature of 60° C. at a speed of four feet per minute. The test strips are then cut and packaged.

While the invention is susceptible to various modifications and alternative forms, specific embodiments thereof have been shown by way of example and were herein described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

We claim:

1. The compound:

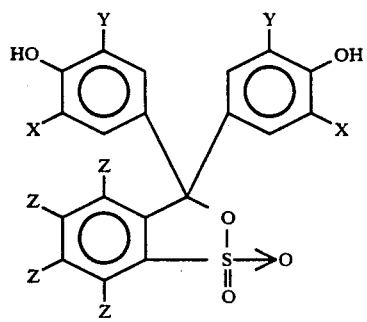

wherein
X is —Cl or —I where Y is —NO$_2$ and X is —Cl, —Br or —I where Y is —NO;
Y is —NO$_2$ or —NO; and
Z is —Cl, —Br, or —I.

2. The compound:

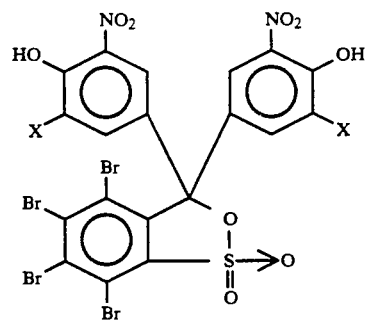

wherein
X is —I, or —Cl.

3. The compound:

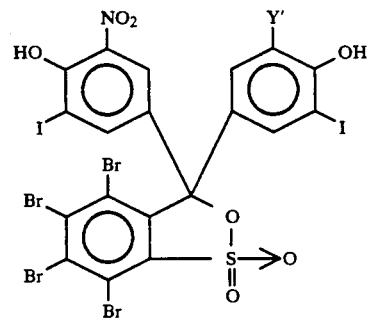

4. The compound:

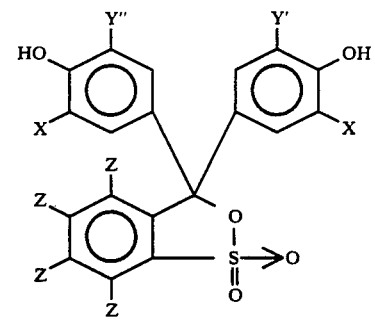

wherein:
X is —I, —Br, or —Cl;
Y' is —NO$_2$, or —NO;
Y'' is —I, —Br, or —Cl; and
Z is —I, —Br, or —Cl.

5. The compound:

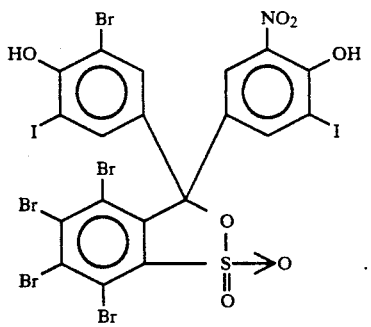

6. An analytical test strip for the detection of protein in a biological sample comprising an absorbent carrier impregnated with the compound:

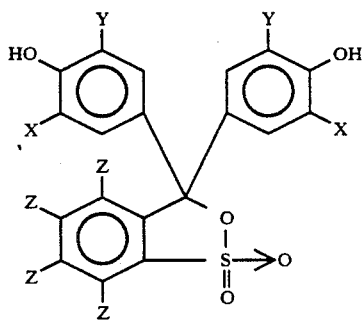

wherein:
X is —I, —Br, or —Cl;
Y is —NO₂ or —NO; and
Z is —I, —Br, or —Cl.

7. An analytical test strip for the detection of protein in a biological sample comprising an absorbent carrier impregnated with the compound:

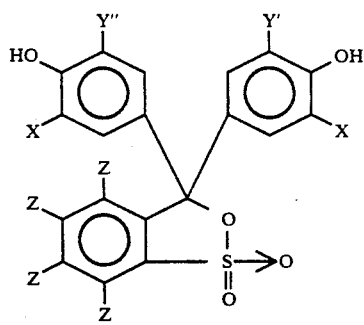

wherein:
X is —I, —Br, or —Cl;
Y' is —NO₂ or —NO;
Y" is —I, —Br, or —Cl; and
Z is —I, —Br, or —Cl.

8. The analytical test strip of claims 6 or 7 wherein the test strip further includes a buffer, and a color enhancing polymer.

9. A method for the detection of protein in a biological sample, the method comprising the steps of:
a) wetting an analytical test strip with the biological sample, the test strip including an absorbent carrier impregnated with the compound:

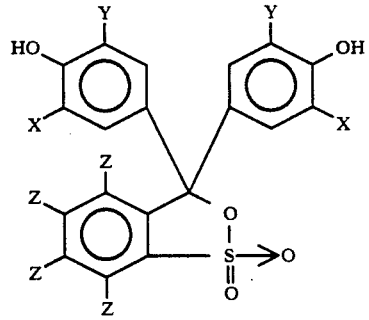

wherein:
X is —Cl, —Br, —I;
Y' is —NO₂ or —NO;
Y" is —Cl, —Br, —I; and
Z is —Cl, —Br, —I; and
b) observing and recording any color change of the test strip, wherein a color change is indicative of protein in the biological sample.

10. A method for the detection of protein in a biological sample, the method comprising the steps of:
a) wetting an analytical test strip with the biological sample, the test strip including an absorbent carrier impregnated with the compound:

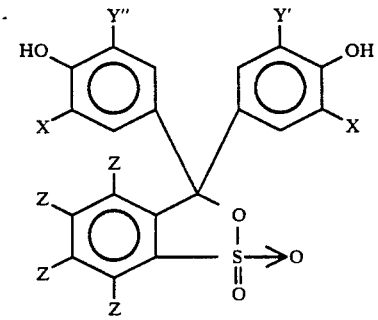

wherein:
X is —Cl, —Br, —I;
Y is —NO₂ or —NO; and
Z is —Cl, —Br, —I; an
b) observing and recording any color change of the test strip, wherein a color change is indicative of protein in the biological sample.

11. The method of claim 9 or 10 wherein said test strip is further impregnated with a buffer and a color enhancing polymer.

* * * * *

UNITED STATES PATENT AND TRADEMARK OFFICE
CERTIFICATE OF CORRECTION

PATENT NO.  : 5,187,104
DATED       : February 16, 1993
INVENTOR(S) : Paul F. Corey, Angela A. Michaels, Lois J. Proud, Michael Salvati, Robert W. Trimmer and Ronald G. Sommer It is certified that error appears in the above-identified patent and that said Letters Patent is hereby corrected as shown below:

Column 16:

Claim 3, Line 2, change "y'" to -- $NO_2$ --.

Signed and Sealed this

Third Day of October, 1995

Attest:

BRUCE LEHMAN

Attesting Officer

Commissioner of Patents and Trademarks